(12) United States Patent
Ippisch (10) Patent No.: US 8,523,845 B2
(45) Date of Patent: *Sep. 3, 2013

(54) METHOD FOR OPERATING A SURGICAL POWER TOOL (75) Inventor: Andreas Ippisch, Merdingen (DE)

(73) Assignee: Stryker Leibinger GmbH & Co. KG (DE)

(*) Notice: Subject to any disclaimer, the term of this patent is extended or adjusted under 35 U.S.C. 154(b) by 513 days.

This patent is subject to a terminal disclaimer.

(21) Appl. No.: 12/699,259

(22) Filed: Feb. 3, 2010

(65) Prior Publication Data
US 2010/0204685 A1    Aug. 12, 2010

(30) Foreign Application Priority Data

Feb. 4, 2009   (EP) .................................. 09001518

(51) Int. Cl.
A61B 17/00      (2006.01)

(52) U.S. Cl.
USPC .............. 606/1; 200/5 E; 200/51.16; 200/510

(58) Field of Classification Search
USPC .............. 606/1; 200/5 R, 5 A, 5 B, 5 C, 5 D, 200/5 E, 5 EA, 5 EB, 5 F, 51.16, 510
See application file for complete search history.

(56) References Cited

U.S. PATENT DOCUMENTS

| | | | |
|---|---|---|---|
| 3,463,990 A | 8/1969 | Ross | |
| 3,742,157 A | 6/1973 | Leposavic | |
| 4,680,831 A * | 7/1987 | Hogan | 452/164 |
| 4,794,215 A | 12/1988 | Sawada et al. | |
| 5,098,430 A | 3/1992 | Fleenor | |
| 5,162,775 A | 11/1992 | Kuramochi et al. | |
| 5,332,944 A | 7/1994 | Cline | |
| 5,561,278 A | 10/1996 | Rutten | |
| 5,626,595 A * | 5/1997 | Sklar et al. | 606/170 |
| 5,982,304 A | 11/1999 | Selker et al. | |
| 5,999,084 A | 12/1999 | Armstrong | |
| 6,003,390 A | 12/1999 | Cousy | |
| 6,020,195 A | 2/2000 | Schmolke et al. | |
| 6,037,724 A | 3/2000 | Buss et al. | |
| 6,064,141 A | 5/2000 | Wiciel | |
| 6,106,524 A | 8/2000 | Eggers et al. | |

(Continued)

FOREIGN PATENT DOCUMENTS

| | | |
|---|---|---|
| CH | 674111 A5 | 4/1990 |
| DE | 102004041871 A1 | 3/2006 |
| EP | 1236439 A2 | 9/2002 |
| EP | 1754447 A2 | 2/2007 |

OTHER PUBLICATIONS

US Non-Final Office Action for U.S. Appl. No. 12/699,249 dated May 29, 2012.

(Continued)

Primary Examiner — Henry M Johnson, III
Assistant Examiner — John R Downey
(74) Attorney, Agent, or Firm — Lerner, David, Littenberg, Krumholz & Mentlik, LLP (57) ABSTRACT A surgical power tool has an actuation assembly which comprises a force sensor and a switch. The force sensor is provided to determine an actuation force produced by the user, and the switch is transferred by the actuation force from a first switching state to a second switching state. A combined evaluation of the force sensor signal and of the switching state enables, for example, a plausibility check for increasing the operational reliability of the power tool.

16 Claims, 6 Drawing Sheets (56) References Cited

U.S. PATENT DOCUMENTS

| | | |
|---|---|---|
| 6,500,169 B1 | 12/2002 | Deng |
| 6,608,270 B2 | 8/2003 | Donofrio et al. |
| 6,945,981 B2 | 9/2005 | Donofrio et al. |
| 7,177,533 B2 | 2/2007 | McFarlin et al. |
| 7,358,654 B2 | 4/2008 | Aromin |
| 7,398,688 B2 | 7/2008 | Zdeblick et al. |
| 7,820,930 B2 | 10/2010 | Mao |
| 2002/0011092 A1 | 1/2002 | Hara et al. |
| 2002/0049464 A1 | 4/2002 | Donofrio et al. |
| 2004/0248262 A1 | 12/2004 | Koeberl et al. |
| 2005/0267329 A1 | 12/2005 | Konstorum et al. |
| 2006/0100485 A1 | 5/2006 | Arai et al. |
| 2007/0096666 A1 | 5/2007 | Ippisch |
| 2007/0119698 A1 | 5/2007 | Day |
| 2009/0096666 A1 | 4/2009 | Ikeda |

OTHER PUBLICATIONS

Barash et al., "Human secretory signal peptide description by hidden Markov model and generation of a strong artificial signal peptide for secreted protein expression", Biochemical and Biophysical Research Communications 294 (2002), 835-842.

Herrera et al., "A family of compact plasmid vectors for DNA immunization in Humans", Biochemical and Biophysical Communications 279, 548-551 (2000).

* cited by examiner

METHOD FOR OPERATING A SURGICAL POWER TOOL

BACKGROUND OF THE INVENTION

The invention relates generally to surgical power tools such as electric-motor-driven drills, bone saws and screwdrivers. To be more precise, the invention relates to a surgical power tool comprising an actuation assembly having a force sensor.

For several decades a wide variety of power tools have been used by surgeons in their work. Conventional surgical power tools frequently comprise mechanical actuation assemblies having slide switches, tumbler switches or rotary knobs for controlling certain functionalities of the tools. However, mechanical actuation assemblies are sometimes disadvantageous for surgical power tools, if the tools have to be sterilized at any rate. This is due to the fact that the moving components of such assemblies are very difficult to seal against the ingress of liquid or gaseous sterilization media.

The penetration of a sterilization medium into mechanical actuation assemblies is detrimental to their operability. For this reason, surgical power tools having tumbler switches, rotary knobs or similar moving components either cannot be sterilized at all or must be serviced after a few sterilization cycles.

To improve the sterilizability of surgical power tools, or to make it possible in the first place, actuation assemblies may be equipped with a force sensor. Force sensors have a planar design and have no moving mechanical elements. For these reasons, force sensors can be installed in a simple and sealed manner below a flexible housing section of a surgical power tool.

Surgical power tools having force sensors arranged below flexible housing sections are known, for example, from U.S. Pat. Nos. 3,463,990 and 6,037,724. In the case of the power tools described in these documents, the respective force sensor is housed within a casing of plastics material which protects the force sensor against sterilization media.

Furthermore, a surgical power tool having a force sensor arranged in a metal capsule is known from U.S. Patent Publication No. 2007/0096666. The encapsulation protects the sensor reliably from sterilization media. To ensure the operability of the encapsulated force sensor, continuous calibration is proposed.

The object on which the invention is based is to increase the operability of known surgical power tools having force sensors.

BRIEF SUMMARY OF THE INVENTION

According to a first aspect, an actuation assembly for the actuation-force-dependent control of the operation of a surgical power tool is proposed, the actuation assembly comprising a force sensor configured to sense the actuation force, and a switch which can be transferred by the actuation force from a first switching state to a second switching state.

Such an actuation assembly may be designed in such a manner that a user-induced actuation force can both change the switching state of the switch and act on the force sensor, when a minimum actuation force value is reached or exceeded at any rate. In this case, the change of the switching state may be effected substantially simultaneously with the action of force on the force sensor, or the change may precede or follow the action of force. The order depends, in the individual case, on the configuration and mutual arrangement of force sensor and switch.

With regard to the construction of the force sensor, a selection may be made between different implementations. For example, it is possible to configure the force sensor as a strain gauge, a piezo element, a semiconductor element, etc. A signal processing circuit electrically coupled to the force sensor may be provided for the force sensor. According to a first variant, the signal processing circuit taps a sensor signal and converts it into a continuous output signal dependent on the actuation force. According to a second variant, the signal processing circuit converts the sensor signal into a discrete, i.e. for example binary (On/Off) or multi-stage, output signal.

The switch may be a two- or multi-stage switch, the switching state of which can be changed by the application of the actuation force. The switch may be configured in such a manner that it automatically resumes the first switching state on removal of the actuation force.

According to a first variant, the switch is arranged upstream of the force sensor in a direction of force transmission. Accordingly, the switch is provided in the force transmission path between a force application point and the force sensor. According to a second variant, the switch is arranged downstream of the force sensor in the direction of force transmission. A third variant provides that the switch and the force sensor lie in parallel force transmission branches. While the force sensor and the switch in the first two variants are arranged one behind the other in the direction of force transmission, according to the third variant both may be arranged, for example, one beside the other (and optionally mechanically coupled to one another).

The actuation assembly may further comprise a circuit which influences the operation of the surgical power tool in dependence on the switching state of the switch. The circuit may further be configured to influence the operation of the surgical power tool additionally in dependence on a force sensor signal. The circuit may comprise one or more functional circuit groups, including a signal processing circuit for the force sensor, a control circuit for an electric motor and a signal evaluation or logic circuit.

According to one configuration, the circuit is configured to disable the operation of the power tool in the first switching state of the switch. The disabling may optionally be effected independently of an actuation force value sensed by the force sensor. Alternatively or additionally to this, the circuit may be configured to enable the operation of the power tool in the second switching state. The operation of the power tool may be effected, for example, in dependence on an actuation force value sensed by the force sensor.

The force sensor may be completely or partially encapsulated. The sensor capsule may be provided for arrangement in, on or under the housing of the surgical power tool. The capsule may consist wholly or partially of a material resistant to sterilization media (or be coated with such a material). For instance, the capsule may be produced wholly or partially from a metal. The capsule may have a covering made of plastic or a core made of a non-metallic material which is covered with a metal coating.

A carrier component for the force sensor may be arranged in a force-transmitting manner between the force sensor and the switch. This carrier component may be part of the sensor capsule housing the force sensor.

The actuation assembly may further comprise a support plate for receiving the sensor capsule. The support plate may be configured to close an opening, formed in a housing of the power tool, for receiving the actuation assembly. The closing of the actuation assembly by the support plate may be effected in a fluid-tight manner in order to counteract the ingress of a sterilization medium into the housing interior. For this purpose, a seal may be provided between the support plate and the housing section delimiting the opening.

To fix and/or center the sensor capsule on the support plate, a bearing component at least partially surrounding the sensor capsule may be used. For this purpose, the bearing component may have a receiving opening for the sensor capsule. The support plate and the bearing component may be produced in one piece or as separate components. It should be pointed out that the support plate and/or the bearing component may be provided independently of the use of a switch.

The switch may comprise two or more contacts. In the case of a switch having at least two contacts, the first contact and the second contact may be kept spaced apart from one another by a spring force. In this way, the effect which can be achieved is that the second switching state is assumed only when the actuation force is sufficient to overcome the spring force.

The first contact may be coupled to the carrier component (i.e. for example a sensor capsule). It is also conceivable for the first contact to be formed by at least one electrically conductive region of the carrier component. The second contact may be formed on a spring plate.

The actuation assembly may further comprise an elastic cover which provides a bearing surface (e.g. for a finger) for the application of the actuation force. The elastic cover may have sealing functions in the region of the actuation assembly or between the actuation assembly and a tool housing which houses the actuation assembly. In this way, the ingress of sterilization media into the actuation assembly and/or into the tool housing can be avoided. The elastic cover may further exhibit damping properties in order to avoid or at least reduce damage to components of the actuation assembly due to impacts or shocks in the surgical environment. For this purpose, the cover may have an increased material thickness at least in regions.

According to a further aspect, a surgical power tool having the actuation assembly described here is proposed. The surgical power tool may further comprise an electric motor for the actuation of a tool element (e.g. a screwdriver blade, a saw blade, a drill bit, etc.). In addition, it is conceivable for the surgical power tool to have more than one actuation assembly. Thus, a first actuation assembly for the operation of the electric motor in a first direction of rotation and a second actuation assembly for the operation of the electric motor in a second direction of rotation opposite to the first direction of rotation may be provided. The two or more actuation assemblies may each have an assigned switch or else may share a common (single) switch.

According to a further aspect, a method for the actuation-force-dependent control of the operation of a surgical power tool is proposed, comprising the steps of sensing a switching state of a switch which can be transferred by the actuation force from a first switching state to a second switching state, interrogating a force sensor configured to sense the actuation force, and controlling the operation of the surgical power tool in dependence on the sensed switching state and in dependence on the sensed actuation force. The switching state may be evaluated in general for checking the plausibility of a signal of the force sensor or for other purposes.

The operation of the surgical power tool may further be controlled in such a manner that the operation of the surgical power tool is disabled in the first switching state, in particular independently of an actuation force value sensed by the force sensor. Additionally or alternatively to this, the operation may take place in the second switching state, in particular in dependence on an actuation force value sensed by the force sensor.

The method may additionally comprise the step of sensing a temperature of the power tool (for example in the housing interior). The operation of the surgical power tool may then be effected in dependence on the sensed temperature. A readiness for operation of the power tool may also be sensed. An acoustic signal may then be emitted in dependence on the sensed readiness for operation. The acoustic signal points out to a user, for example, a lack of readiness for operation of the power tool.

BRIEF DESCRIPTION OF THE DRAWINGS

Further aspects and advantages of the invention will become apparent from the following description of preferred exemplary embodiments and from the figures, in which.

DETAILED DESCRIPTION

Exemplary embodiments of surgical power tools, of an actuation assembly provided therefor, and of an operating method suitable therefor are explained below. Corresponding elements are provided with corresponding reference symbols.

Figure 1:
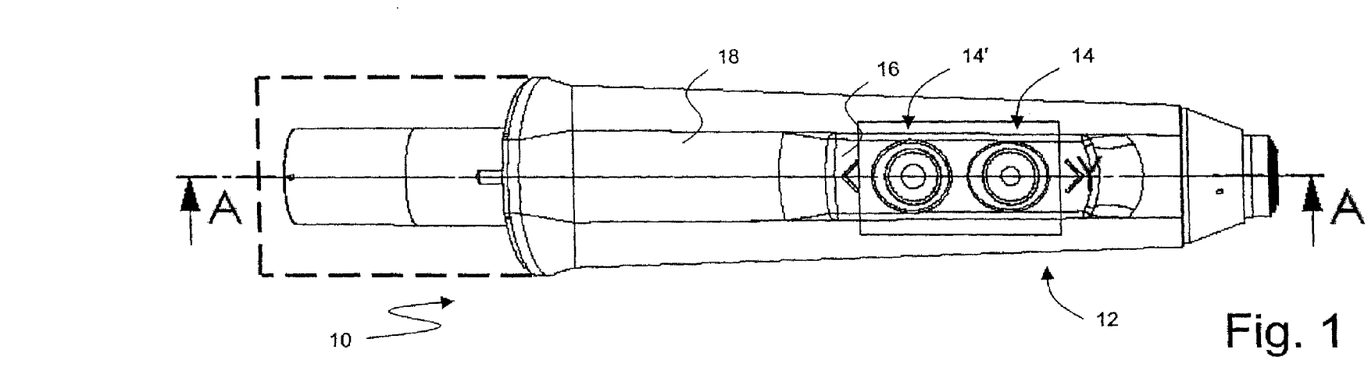
FIG. 1 shows a top view of an exemplary embodiment of a surgical power tool in the form of a screwdriver.

FIG. 1 shows a plan view of a surgical power tool 10 in the form of a battery-operated screwdriver. The surgical power tool 10 has an elongated, approximately cylindrical housing 12 made of aluminium, onto the rear side of which a battery pack (shown only schematically and in broken lines) can be plugged removably.

In the exemplary embodiment, the surgical power tool 10 comprises two actuation assemblies 14, 14' for controlling different tool functions. The actuation assemblies 14, 14' are provided in a front region of the housing 12 which is remote from the battery pack. As can be seen in particular from the sectional view illustrated in FIG. 2 along the line A-A of FIG. 1, the actuation assemblies 14, 14' are received in a collar 16 of the housing 12 which projects from a cylindrical wall region 18 of the housing 12. The collar 16, which is produced in one piece with the wall region 18, surrounds the actuation assemblies 14, 14' laterally and protects them from mechanical influences. On its upper side, the collar 16 has two circular openings 16A, 16A' in order to allow a user to access the actuation assemblies 14, 14'.

Figure 2:
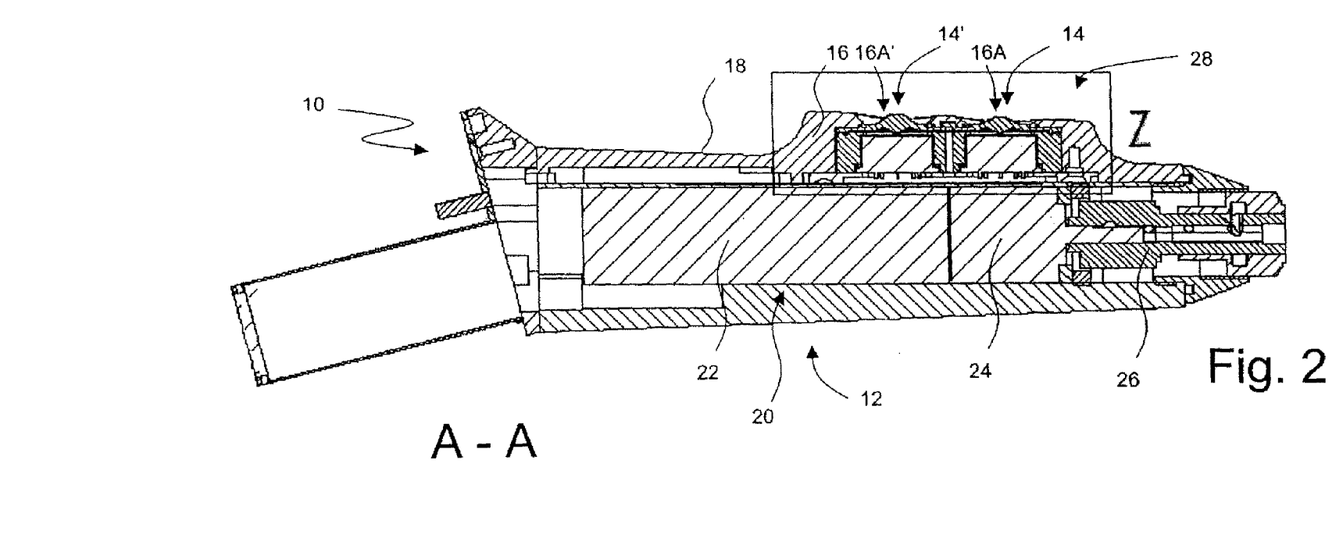
FIG. 2 shows a partial-sectional view of the surgical power tool according to FIG. 1 along the line A-A.

As shown in FIG. 2, an assembly 20 having an electronically commutated motor 22 and a transmission 24 coupled to the motor 22 is provided in the interior of the housing 12. A first of the two actuation assemblies 14, 14' controls the electric motor 22 in a first direction of rotation. The other of the actuation assemblies 14, 14' controls the electric motor 22 in a second direction of rotation opposite to the first direction of rotation. The motor speed in the forward and reverse directions is regulated in each case proportionally to the actuation force applied to the respective actuation assembly 14, 14'. The higher the actuation force, the higher is therefore the motor speed. To regulate the speed, a motor control circuit is provided on a printed circuit board (not shown) fixed in the rear portion of the housing 12.

In addition, a coupling 26 is housed in the housing 12 downstream of the transmission. The coupling 26 permits in known fashion the rotationally fixed coupling of an exchangeable screwdriver blade (not shown) to the transmission 24. An optional locking button (likewise not shown) enables rotationally fixed mechanical locking of the coupling 24. When the locking button is actuated, the power tool 10 can be used in the manner of a conventional screwdriver. In this case, the torque is not generated by the motor 22 but by manual rotation of the housing 12.

Figure 3:
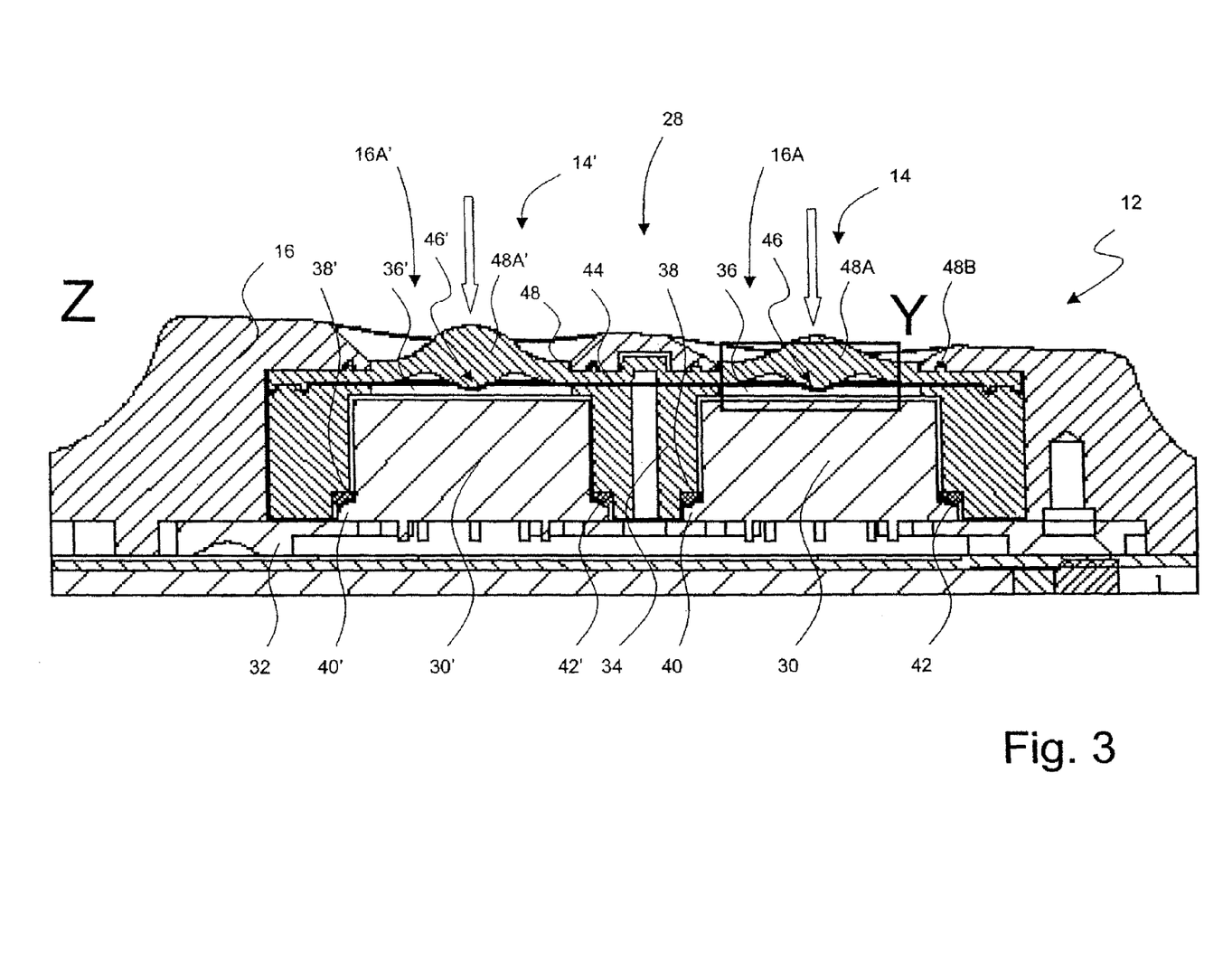
FIG. 3 shows an enlargement of the detail Z of the sectional view according to FIG. 2, illustrating in particular an exemplary embodiment of an actuation unit comprising two actuation assemblies.

The total of two actuation assemblies 14, 14' of the surgical power tool have the same construction and together form an actuation unit 28 which can be handled independently and inserted as a subassembly into the housing 12. FIG. 3 shows the actuation unit 28 in an enlargement of the detail Z of the sectional view according to FIG. 2.

As can be seen in FIG. 3, the actuation assemblies 14, 14' each comprise a sensor capsule 30, 30' made of metal for hermetic encapsulation of a respective force sensor (not shown in FIG. 3). The sensor capsules 30, 30' are arranged on a common support plate 32 which closes a housing opening formed on the lower side of the collar 16. The sensor capsules 30, 30' are fixed on the support plate 32 by means of a common bearing component 34 which centers the sensor capsules 30, 30'. For this purpose, the bearing component 34, of block-shaped form, has two cylindrical bores 36, 36' for receiving a respective sensor capsule 30, 30'. The bearing component 34 consists of an insulating material such as plastic or is otherwise electrically insulated from the metal sensor capsules 30, 30'.

The bores 36, 36' in the bearing component 34 are formed as through-openings and permit access to electrical contacts of the sensor capsules 30, 30' from below and the application of an actuation force to the sensor capsules 30, 30' from above. Furthermore, the bores 36, 36' have a stepped profile with a respective circumferential shoulder 38, 38' which acts as a seat for a diameter enlargement 40, 40' of each sensor capsule 30, 30'. Provided between each shoulder 38, 38' and diameter enlargement 40, 40' is a seal 42, 42' in the form of a silicone ring. The seals 42, 42' prevent the ingress of a sterilization medium along the side walls of the sensor capsules 30, 30' and the inner walls of the bores 36, 36' in the direction of the support plate 32 and the interior of the tool housing 12. In addition, the seals 42, 42' center the sensor capsules 30, 30' on the mounting of the latter in the bearing component 34. For this purpose, the seals 42, 42' may have a suitable profiling (e.g. a thickness decreasing in the direction of the axis of the bores 36, 36').

Provided on the upper side of the bearing component 34 are a planar spring plate 44 and an elastic cover 48 made of silicone or another suitable material. The cover 48 is arranged sealingly between an undercut of the collar 16 and an upper side of the bearing component 34 and thus prevents the ingress of sterilization media through the housing openings 16A, 16A' into the interior of the collar 16 and into the tool housing 12.

In order to optimise the sealing action, the cover has a plurality of surface profilings arranged concentrically with respect to the housing openings 16A, 16A' (in FIG. 3, only a single surface profiling 48B is marked, for the sake of clarity). The surface profilings of the cover 48 are formed as circular projections and cooperate in a form-fitting manner with assigned surface profilings of the collar and of the bearing component 34 in the form of corresponding indentations. The form fit which thus results counteracts the ingress of sterilization media in a direction parallel to the cover 48.

In order to protect the sensor capsules 30, 30' (and the force sensors housed therein) from impacts and shocks in the surgical environment, each of the two actuation assemblies 14, 14' has a respective mechanical damping member 48A, 48A' which is arranged upstream of the sensor capsules 30, 30' in the direction of force application. The direction of force application is illustrated in FIG. 3 by a block arrow for each of the actuation assemblies 14, 14'.

The mechanical damping members 48A, 48A' are integrated into the cover 48 in the exemplary embodiment shown in FIG. 3. To be more precise, the damping members 48A, 48A' are formed as convex increases in thickness of the cover 48 above the central region of each of the two sensor capsules 30, 30'. Owing to the convex shaping, the damping members 48A, 48A' define a region of application for the actuation force which is haptically readily detectable by the user. In the exemplary embodiment according to FIG. 3, the damping members 48A, 48A' have a material thickness of approximately 2.5 to 3.5 mm in their thickest region.

As can be seen in FIG. 3, the spring plate 44 is arranged between the cover 48 and the upper sides of the sensor capsules 30, 30'. With respect to each of the two actuation assemblies 14, 14', the spring plate 44 is part of respective switch 46, 46'. To be more precise, the spring plate 44 provides a respective first contact for each switch 46, 46'. The respective second switching contact is provided by the (metal) upper sides of the sensor capsules 30, 30'. In the first switching state of the switches 46, 46' shown in FIG. 3, the two respective switching contacts are kept spaced apart from one another by the spring force of the spring plate 44. The two switches 46, 46' are thus in an open switching state.

Figure 4:
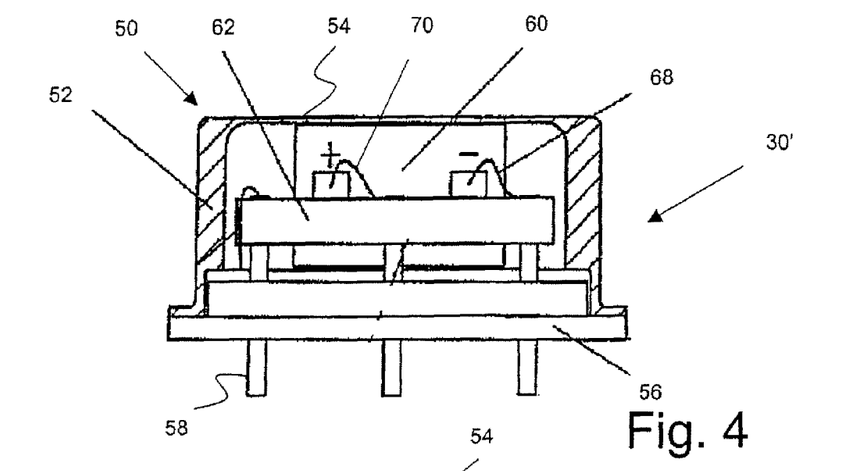
FIG. 4 shows a schematic partial-sectional view of a sensor capsule of one of the actuation assemblies according to FIG. 3.

In what follows, the construction of the sensor capsules 30, 30' and of the switches 46, 46' is explained in more detail with reference to FIGS. 4 to 9. FIG. 4 shows a partial-sectional view of the sensor capsule 30 of the actuation assembly 14. The capsule 30 has a substantially pot-shaped cap 50 made of special steel, which is shown again individually in FIG. 5. The cap 50 comprises a cylindrical wall section 52 and a cover section 54 formed in one piece with the wall section 52. The internal diameter of the wall section 52 is approximately 11 mm (typically approximately 5 to 30 mm) and the height of the wall section 52 is approximately 7 mm (typically approximately 2 to 12 mm). The cover section 54 closes the, in FIG. 4 upper, end side of the wall section 52. The open lower end side of the cap 50 is closed by a cap base 56 hermetically against sterilization media. The cap base 56 likewise consists of special steel.

A plurality of through-openings (not shown) are formed in the cap base 56. A gold-plated electrical contact 58 extends through each through-opening. To stabilise the contacts 58 on the one hand and to ensure a high degree of sealing on the other hand, the openings in the cap base 56 are hermetically closed by means of glass.

Figure 5:
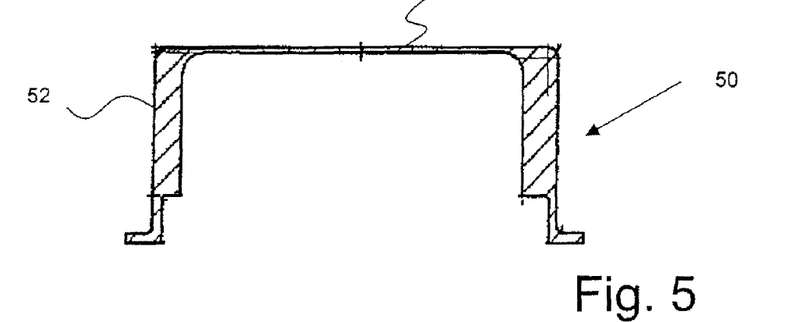
FIG. 5 shows a sectional view of a housing of the sensor capsule according to FIG. 4.

While the cover section 54 has a thickness of approximately 0.3 mm at most, the wall section 52 has a thickness of at least approximately 0.8 mm or more (cf. FIG. 5). Such a design is advantageous in restricting to the cover section 54 the elastic deformation resulting from application of an actuation force to, the cover section 54. In other words, the wall section 52 behaves in a substantially rigid manner with respect to the actuation force applied to the cover section 54. This facilitates the hermetically sealed installation of the sensor capsule 30 in the actuation assembly 14 and in the housing 12 of the power tool 10.

Figure 6:
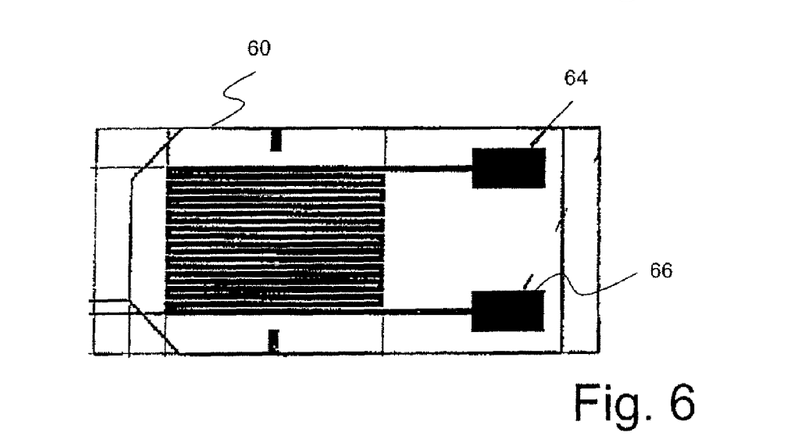
FIG. 6 shows a top view of a force sensor used in each of the actuation assemblies according to FIG. 3, in the form of a strain gauge.

A force sensor 60 and a signal processing circuit 62 for the force sensor 60 are housed inside the capsule 50. FIG. 6 shows a top view of the force sensor 60. The force sensor 60 comprises a planar strain gauge configured in meandering form and having two contacts 64, 66. In the finished, mounted state, the contacts 64, 66 are electrically connected to the signal processing circuit 62. Mounting of the force sensor 60 flat on the inner side of the cover section 54 can be effected by adhesive bonding.

As shown in FIG. 4, the force sensor 60 is coupled to the signal processing circuit 62 by means of electrical contactings 68, 70. The signal processing circuit 62 is in turn electrically contacted by the contacts 58 leading out of the capsule 30.

Figure 7:
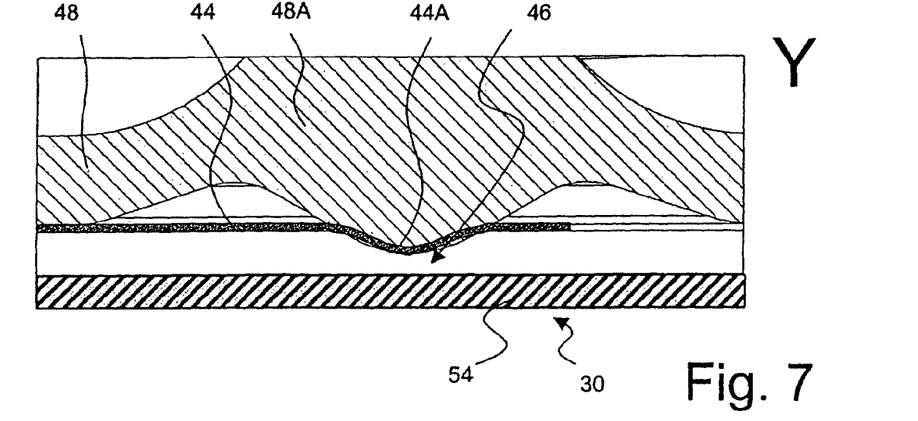
FIG. 7 shows an enlargement of the detail Y of the sectional view according to FIG. 3, illustrating in particular the operation of a switch.

The construction of the switches 46, 46' is now described with reference to FIGS. 7 to 9. In this regard, reference is first made to FIG. 7 and the enlargement of the detail Y in FIG. 3 shown there. The construction of the switch from a first switching contact 44A formed on the spring plate 44 and from a second switching contact formed by the metal cover section 54 of the sensor cap 50 can be clearly seen in FIG. 7.

Figure 8:
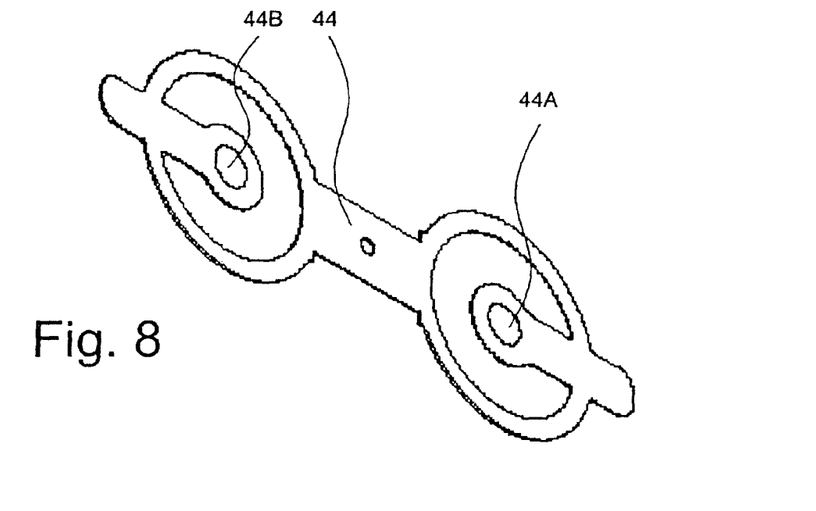
FIG. 8 shows a perspective view of a spring plate used in the switch according to FIG. 7.

As can be seen from the shaping of the spring plate illustrated in FIG. 8, the switching contact 44A of the switch 46 is formed by a tongue-shaped spring plate section which is connected at one location to an annular further spring plate section. The annular spring plate section lies on the bearing component 34 shown in FIG. 3, while the tongue-shaped spring plate region (with the switching contact 44A) is deflectable perpendicularly to the plane of the spring plate against a spring force. This deflection takes place in an elastically reversible manner, so that following a deflection the spring plate 44 assumes its original planar form again.

Figure 9:
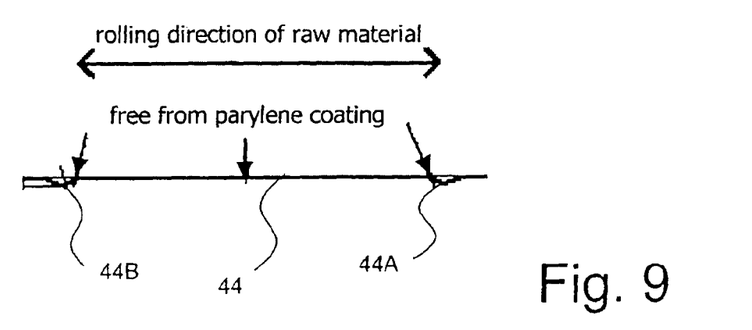
FIG. 9 shows a side view of the spring plate according to FIG. 8.

FIG. 9 shows a side view of the spring plate 44. The rolling direction during production of the spring plate 44 is further indicated in FIG. 9 by an arrow. The spring plate 44 is coated on both sides with an electrically insulating material such as, for example, parylene. Only three contact locations are left free from this coating, namely the switching contact 44A, a corresponding switching contact 44B of the second actuation assembly 14' and a contact region which is formed in the center of the spring plate 44 and via which a circuit is closed. As shown in FIGS. 7 and 9, the switching contact 44A has a concavely curved shape in order to establish a defined, point contact closure between the switching contact 44A and the switching contact lying opposite in FIG. 7 in the form of the cover section 54.

The operation of the actuation assembly 14 is now explained in more detail with reference to FIGS. 3, 4 and 7. It will be understood that the following statements also apply to the operation of the second actuation assembly 14'.

When an actuation force is applied (for example by finger pressure) to the readily palpable thickened section 48A of the elastic cover 48, the latter is displaced in the direction of the housing interior. Also involved in this displacement of the cover 48 is the switching contact 44A shown in FIG. 7, which in the initial state lies against the cover 48. To be more precise, the switching contact 44A is displaced in the direction of the cover section 54 against the spring force provided by the spring plate 44. After a displacement travel of approximately 0.5 mm (typically about 0.1 to 2 mm), the switching contact 44A comes into contact with the cover section 54. As a result of this coming into contact, the switch 46 is closed, i.e. it is transferred from an open state to a closed state. The closing of the switch 46 at the same time causes the closing, detectable by means of a logic circuit, of a circuit comprising the spring plate 44 and the sensor capsule 30 as conducting elements. In an alternative embodiment (not shown), the switch 46 is configured to be opened by the actuation force.

As soon as the switching contact 44A has come into contact with the cap cover 54, a further increase of the actuation force causes an actuation force component to be applied to the cover section 54. The upper side of the cover section 54 permits the take-up of this actuation force component. The cover section 54 thereupon deforms elastically in the direction of the interior of the capsule 30. This deformation of the cover section 54 is transmitted to the force sensor 60, which is fastened to the lower side of the cover section 54 (cf. FIG. 4). To be more precise, the deformation causes stretching of the force sensor 60 configured as a strain gauge. As a result of this stretching, the resistance of the force sensor 60 changes. This change of resistance of the force sensor 60 in turn displaces the operating point of a bridge circuit which comprises the force sensor 60 and together with an amplifier circuit forms the signal processing circuit 62. The force sensor 60 is part of the bridge circuit, which, in addition to three further bridge resistors, also comprises two balancing resistors. A suitable circuit is known, for example, from EP 1 754 447 A2.

The displacement of the operating point is detected by the amplifier circuit, in the form of a differential amplifier, of the signal processing circuit 62 and converted into an amplified difference signal. The amplified difference signal is provided by the signal processing circuit 62 as an output signal for further processing. The level of the output signal is proportional to the deformation of the strain gauge and therefore also proportional to the actuation force applied to the cover section 54. In an alternative embodiment, the signal processing circuit is so configured that the output signal has two or more discrete levels (for example, in dependence on the exceeding of one or more force thresholds).

A motor control circuit is electrically coupled to the signal processing circuits of the actuation assemblies 14, 14'. A logic circuit is arranged functionally between the motor control circuit and the two actuation assemblies 14, 14'. The logic circuit has essentially the effect that with simultaneous application of force to both actuation assemblies 14, 14' no undefined state is produced. For this purpose the logic circuit has two separate input connections, each of which is coupled to one of the two actuation assemblies 14, 14'. If a signal is supplied to only one of the two input connections, an amplified output signal is transmitted to the motor control circuit via exactly one of two output connections. A signal for the first direction of rotation is supplied to the motor control circuit via a first control connection and a signal for the second, opposite direction of rotation via a second control connection.

If output signals are supplied to both input connections of the logic circuit (i.e. if an actuation force is applied to both actuating assemblies 14, 14'), the logic implemented in the logic circuit causes no output signal to be delivered from either of the two output connections to the motor control circuit. In addition, a "brake" connection assumes a high signal level. The high signal level at the "brake" connection short-circuits the electronically commutated electric motor 22, whereby the electric motor 22 is electrically braked and brought to a standstill. The logic circuit also comprises a speed regulation output. Via the speed regulation output, the motor control circuit receives feedback regarding the required motor speed. A suitable logic circuit is known, for example, from EP 1 754 447 A2. The known logic circuit may be further supplemented with logic elements which link the output signals of the switches 46, 46' and of the output connections explained above (e.g. by means of an AND operation), in order to implement the plausibility check explained below.

Figure 10A:
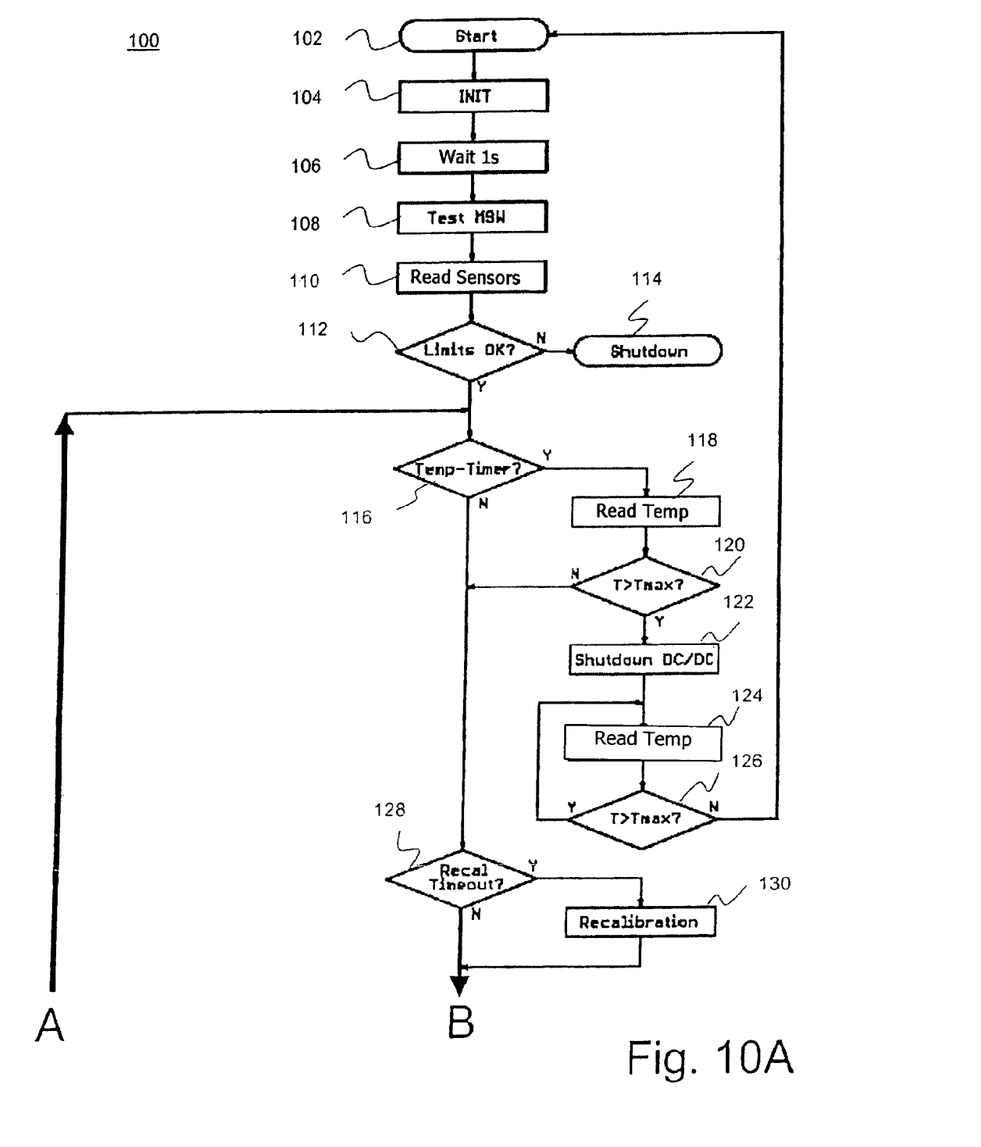
FIGS. 10A/B show a schematic flow chart, illustrating an exemplary embodiment of a method for operating the surgical power tool.
Figure 10B:
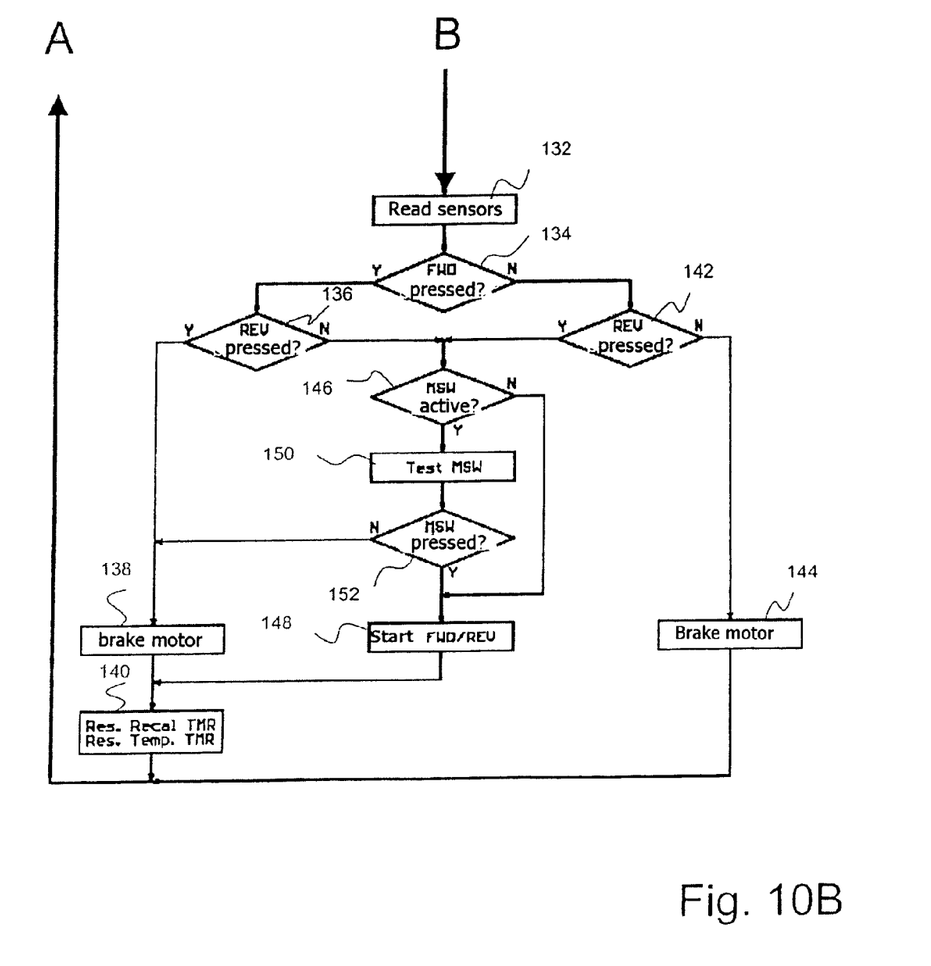

In what follows, the operation of the surgical power tool 10 is described in more detail with the aid of the schematic flow chart 100 according to FIGS. 10A and 10B. The operating method begins in step 102 with the plugging of a battery pack onto the tool base body shown in FIG. 1 and the accompanying initialization of the individual tool circuits in step 104. Following the initialization step 104 and a waiting time (step 106), the operability of the two switches 46, 46' (also called main switches or "MSW" below) is checked in step 108. This involves in particular checking whether both switches 46, 46' are in their open switching state shown in FIG. 3. If one of the two switches 46, 46' is in a closed switching state already in the initialization state of the power tool 10, this indicates a malfunction (for example a bent spring plate 44 or fluid ingress).

At the same time as or at a time interval from the testing of the switches 46, 46', the force sensor signals of the actuation assemblies 14, 14' are read out in step 110. In a following checking step 112, it is determined whether the output signals of the force sensors lie within a preset range (e.g. above preset lower limits and below preset upper limits). Undershooting a lower limit or overshooting an upper limit in the initialization state indicates a malfunction (for example a plastic deformation of a cover section 54). If it is established in step 112 that the lower limit is undershot or the upper limit is overshot for at least one of the force sensors or that one of the switches 46, 46' is in a closed state, the method branches to step 114 and operation of the power tool 10 is blocked. An acoustic signal indicating the malfunction can be simultaneously emitted.

If, in contrast, no malfunction is found in step 112, the method continues with a checking step 116. In step 116 it is determined whether a first timer, which has been started for example during a preceding operating process or in the initialization step 104, has elapsed. If it is established in step 116 that the first timer has elapsed, the method branches to step 118 and a temperature sensor arranged in the housing interior is read out. The temperature sensor is arranged on the printed circuit board of the motor control circuit close to the temperature-sensitive electronic components. Subsequently, the read-out temperature value is compared with a temperature upper limit $T_{max}$ of for example 80° in the checking step 120. In general, the temperature upper limit may lie in a range between 60° and 100°.

If the temperature value lies above the temperature upper limit, in step 122 the operation of the power tool 10 is temporarily blocked to prevent failure or destruction of electronic components. Simultaneously, the temporary blockage of the operation is indicated by an acoustic signal (which differs from the acoustic signal of step 114). Then, in steps 124 and 126 the temperature is read out once again and compared with the temperature upper limit $T_{max}$. The two steps 124 and 126 are carried out until the temperature upper limit is no longer overshot. As soon as this case occurs, the method branches from step 126 back to step 102.

If, on the other hand, in step 120 it is established that the temperature upper limit is not overshot, or the first timer (step 116) has not yet elapsed, the operating method is continued with a step 128 in which a second timer is read out. The second timer, which was likewise started for example with the last operating process or in the initialization step 104, presets the valid period of time for an earlier sensor calibration. If it is determined that this period of time has elapsed, a recalibration of the force sensors is carried out in step 130. The recalibration in step 130 can take into account the force values read out in step 110 and include an adaptation, based on these force values, of the corresponding upper limits for the checking in step 112. If it is determined in step 128 that no recalibration is required, or if a recalibration has been carried out in step 130, the operating method is continued with step 132.

In step 132 the force sensors of the two actuation assemblies 14, 14' are read out again. As already explained above, a first actuation assembly 14 controls the drive of the electric motor 22 in a first direction of rotation ("FWD"), while the second actuation assembly 14' controls the operation of the electric motor 22 in the opposite direction of rotation ("REV").

After the sensor values have been read out in step 132, it is checked in step 134 whether the force sensor of the actuation assembly 14 delivers an actuation signal ("FWD"). If this is the case, it is determined in a following step 136 whether the force sensor of the other actuation assembly 14' likewise delivers an actuation signal ("REV"). If it is established in steps 134 and 136 that the force sensors of both actuation assemblies 14, 14' deliver actuation signals, it is concluded, as explained above, that an undefined actuation state is present, since both actuation assemblies 14, 14' are actuated. Thereupon, in step 138 braking of the electric motor 22 takes place as discussed above in connection with the logic circuit. If the electric motor 22 is still not running at all, the electric motor 22 remains in this state. Following step 138, the two timers for the temperature check and the checking for a required recalibration are reset in step 140. The operating method then branches back to step 116.

If it is established in step 134 that the force sensor of the actuation assembly 14 has not been pressed and if, furthermore, it can be determined in step 142 that the force sensor of the further actuation assembly 14' has not been pressed either, braking of the electric motor 22 takes place in step 144 analogously to step 138, and the method continues with the checking step 116. If, in contrast, it is determined in the steps 136, 142 that only one of the two force sensors of the actuation assemblies 14, 14' delivers an actuation signal, it is checked in step 146 whether an operating mode has been selected in which a plausibility check of the force sensor signals by means of the switching state of the switches 46, 46' has been selectively deactivated. In the case of a deactivated plausibility check, the operating method branches from step 146 to step 148, and the electric motor 22 is started in the required direction of rotation ("FWD"/"REV"). The motor speed is then regulated in dependence on the signal delivered by the corresponding actuation assembly 14, 14' (i.e. in dependence on the actuation force).

If, on the other hand, it is established in step 146 that an operating mode is activated in which a plausibility check takes place by evaluation of the switching state of the corresponding switch 46, 46', it is determined in the steps 150 and 152 whether the switch 46, 46' which is assigned to the actuation assembly 14, 14' delivering the actuation signal is in its closed switching state. If this is not the case, this points to a malfunction since it is not plausible that, when the switch 46, 46' is open, the force sensor of the assigned actuation assembly 14, 14' delivers an actuation signal. For this reason, the method in this case branches from step 152 to step 138 and the electric motor 22 is braked or not even started at all.

If, on the other hand, in the course of the plausibility check in step 152 it is determined that the switch 46, 46' which is assigned to the actuation assembly 14, 14' delivering the actuation signal is in its closed state, the plausibility check is successfully concluded and the electric motor is started in step 148 in the required direction of rotation. In addition, its speed is regulated in dependence on the actuation force.

The surgical power tool 10 described affords increased operational reliability owing to the switches 46, 46' provided in addition to the force sensors, since implausible operating states can be reliably detected. Such implausible operating states may be accompanied, for example, by a plastic deformation of the sensor capsules 30, 30' due to shocks or impacts. To be precise, in the event of a plastic deformation, the associated force sensor may deliver a signal which could be erroneously interpreted as an actuation signal. However, the evaluation of the switching state of the switches 46, 46' is not restricted to the plausibility check explained above.

In order to avoid a plastic deformation of the sensor capsules 30, 30' as far as possible, a mechanical damping member 48A, 48A' is arranged upstream of each sensor capsule 30, 30' in the direction of force application. In the exemplary embodiment described here, the damping members 48A, 48A' are integrated, as convex increases in thickness, into the cover 48 and thus define a haptically readily detectable force application region. In other embodiments, it would be conceivable to provide the damping members below the cover 48 (e.g. between the cover 48 and each sensor capsule 30, 30').

Further advantages of the power tool 10 described here consist in the improved sealing of the housing interior with respect to sterilization media. This improved sealing is attributable, for example, to the provision of additional sealing elements such as the annular seals 42, 42' and to the sealing function of the cover 48 and the support plate 32. Further advantages result from the overall increased stability of the actuation assemblies 14, 14' which is attributable, inter alia, to the use of the support plate 32 and the bearing component 34. It is obvious to a person skilled in the art that these various functionalities and advantages may be realised independently of one another. Thus, for example, the improved sealing functions and the increased stability can be realised independently of the use of the switches 46, 46'.

Self-evidently, the field of application of the actuation assembly presented here is not limited to a surgical power tool in the form of a screwdriver. Rather, an actuation assembly can also be used in other surgical power tools, such as drills, saws, etc.

Numerous modifications and additions relating to the actuation assembly according to the invention and to the surgical power tool according to the invention are therefore possible. The scope of the invention is limited solely by the range of protection of the following claims.

The invention claimed is:

1. An actuation assembly for the actuation-force-dependent control of the operation of a surgical power tool, comprising
    a force sensor configured to sense the actuation force and produce an output signal;
    a switch which can be transferred by the same actuation force sensed by the force sensor from a first switching state to a second switching state;
    a circuit which influences the operation of the surgical power tool in dependence on the switching state of the switch;
    wherein an actuation assembly is designed in such a manner that a user-induced actuation force at the same time changes both the switching state of the switch and acts on the force sensor, and the circuit is further adapted to allow operation of the surgical tool based on the output signal of the force sensor only if the switching state of the switch has changed from the first to the second switching state.

2. The actuation assembly according to claim 1, wherein the switch is arranged proximal to the force sensor in a direction of force transmission.

3. The actuation assembly according to claim 1, wherein the circuit is configured
    to disable the operation of the power tool in the first switching state, in particular independently of an actuation force value sensed by the force sensor; and
    to enable the operation of the power tool in the second switching state, in particular in dependence on an output signal proportional to the actuation force value sensed by the force sensor.

4. The actuation assembly according to claim 1, further comprising a carrier component for the force sensor which is arranged in a force-transmitting manner between the force sensor and the switch.

5. The actuation assembly according to claim 4, wherein the carrier component is part of a sensor capsule housing the force sensor.

6. The actuation assembly according to claim 4, wherein the first contact is coupled to the carrier component or formed by the carrier component.

7. The actuation assembly according to claim 1, wherein the switch comprises a first contact and a second contact, the first contact and the second contact being kept spaced apart from one another by a spring force in the first switching state.

8. The actuation assembly according to claim 7, wherein the second contact is formed on a spring plate.

9. A surgical power tool, comprising at least one actuation assembly according to claim 1.

10. The surgical power tool according to claim 9 further comprising an electric motor, a first actuation assembly for the operation of the electric motor in a first direction of rotation and a second actuation assembly for the operation of the electric motor in a second direction of rotation.

11. An actuation assembly, for the actuation-force-dependent control of the operation of a surgical power tool, comprising
    a force sensor configured to sense an actuation force and produce an output signal proportional to the force sensor;
    a switch associated with the force sensor which can be transferred from a first switching state to a second switching states by the same actuation force sensed by the force sensor; and
    a circuit which operates the surgical power tool depending on both the switching state of the switch and, at the same time, the output signal produced by actuation force sensed by the force sensor, wherein the circuit will not operate the tool unless the switch is in the second switching state independently of the force sensor output signal.

12. The actuation assembly according to claim 11 wherein the switch is arranged proximal of the force sensor in a direction of force transmission.

13. The actuation assembly according to claim 11 wherein the circuit is configured to disable the operation in the first switching state, in particular independently of an actuation force value sensed by the force sensor and to enable the operation in the second switching state, in particular in dependent on an actuation force value sensed by the force sensor.

14. The actuation assembly according to claim 11, further comprising a carrier component for the force sensor which is arranged in a force-transmitting manner between the force sensor and the switch.

15. The actuation assembly according to claim 11, wherein the switch comprises a first contact and a second contact, the first contact and the second contact being kept spaced apart from one another by a spring force in the first switching state.

16. An actuation assembly for the control of the operation of a surgical power tool, comprising first and second actuators independently operable by a force applied by a user, the first actuator capable of causing operation of the power tool in a first rotational direction and the second actuator capable of causing operation of the power tool in an opposite rotational direction, each actuator comprising:

a force sensor for sensing the force applied by the user and producing an output signal proportional to the force sensed;

a switch associated with the force sensor which can be transferred from a first switching state to a second switching state by the force applied by the user;

a circuit which contacts the operation of the power tool depending on which of the first and second actuators are activated based on an output of the associated force sensor and the switching state of the associated switch wherein the power tool is not operated by the force sensor if both the first and second actuator sense a force or if the switching state of the switch has not changed from the first to the second switching state independently of the output of the associated force sensor.

* * * * *